(12) United States Patent
Kawaguchi et al.

(10) Patent No.: US 8,697,136 B2
(45) Date of Patent: Apr. 15, 2014

(54) TRANSGLUTAMINASE CROSSLINKED PROTEIN MICROPARTICLE FILM COMPOSITION

(75) Inventors: Haruma Kawaguchi, Yokohama (JP); Akiko Sudo, Yokohama (JP); Yuichiro Mori, Yokohama (JP); Katsuhiko Yagi, Yokohama (JP); Takashi Oka, Yokohama (JP)

(73) Assignees: Shiseido Company, Ltd., Tokyo (JP); Keio University, Tokyo (JP)

( * ) Notice: Subject to any disclaimer, the term of this patent is extended or adjusted under 35 U.S.C. 154(b) by 507 days.

(21) Appl. No.: 12/735,410

(22) PCT Filed: Jan. 14, 2009

(86) PCT No.: PCT/JP2009/050393
§ 371 (c)(1),
(2), (4) Date: Jul. 14, 2010

(87) PCT Pub. No.: WO2009/090962
PCT Pub. Date: Jul. 23, 2009

(65) Prior Publication Data
US 2011/0044928 A1 Feb. 24, 2011

(30) Foreign Application Priority Data
Jan. 15, 2008 (JP) .................... 2008-006117

(51) Int. Cl.
*A61K 9/50* (2006.01)
(52) U.S. Cl.
USPC ........................................ 424/499
(58) Field of Classification Search
None
See application file for complete search history.

(56) References Cited

U.S. PATENT DOCUMENTS

| 5,525,336 | A | | 6/1996 | Green et al. |
| 5,679,377 | A | * | 10/1997 | Bernstein et al. ............. 424/491 |
| 2008/0286364 | A1 | | 11/2008 | Ogiwara et al. |
| 2008/0299159 | A1 | | 12/2008 | Aimi et al. |
| 2009/0004278 | A1 | | 1/2009 | Aimi et al. |

FOREIGN PATENT DOCUMENTS

| JP | 61-152247 A | 7/1986 |
| JP | 61-172807 A | 8/1986 |
| JP | 62-074360 A | 4/1987 |
| JP | 02-169511 A | 6/1990 |
| JP | 07-215894 A | 8/1995 |
| JP | 08-506830 A | 7/1996 |
| JP | 2006-348012 A | 12/2006 |
| JP | 2007-224012 A | 9/2007 |
| JP | 2008-189784 A | 8/2008 |
| JP | 2008-285432 A | 11/2008 |
| JP | 2008-297241 A | 12/2008 |
| WO | WO 94/18945 A1 | 9/1994 |
| WO | WO 99/11196 A1 | 3/1999 |

OTHER PUBLICATIONS

International Search Report mailed Apr. 21, 2009, in PCT/JP2009/050393, 2 pages.

(Continued)

*Primary Examiner* — Carlos Azpuru
(74) *Attorney, Agent, or Firm* — Foley & Lardner LLP

(57) ABSTRACT

The present invention provides a film composition effective for correcting irregularities on the skin surface, which has stretchability and flexibility as a result of crosslinkable protein microparticles in the film composition being crosslinked by transglutaminase, as well as superior air permeability and moisture evaporation properties as a result of forming a film with the crosslinkable protein microparticles.

25 Claims, 6 Drawing Sheets

(56) References Cited

OTHER PUBLICATIONS

Food Chemistry, 2001, 22(1):73-75, with partial English translation (p. 73, right column, lines 3-7), and English abstract on last page.

Mingyu et al., "Transglutaminase and its Application in Food Industry," China Food Additives, 2004, 5:81-88, with partial English translation (p. 82, right column, lines 2-10 from the bottom), and English abstract on first page.

* cited by examiner

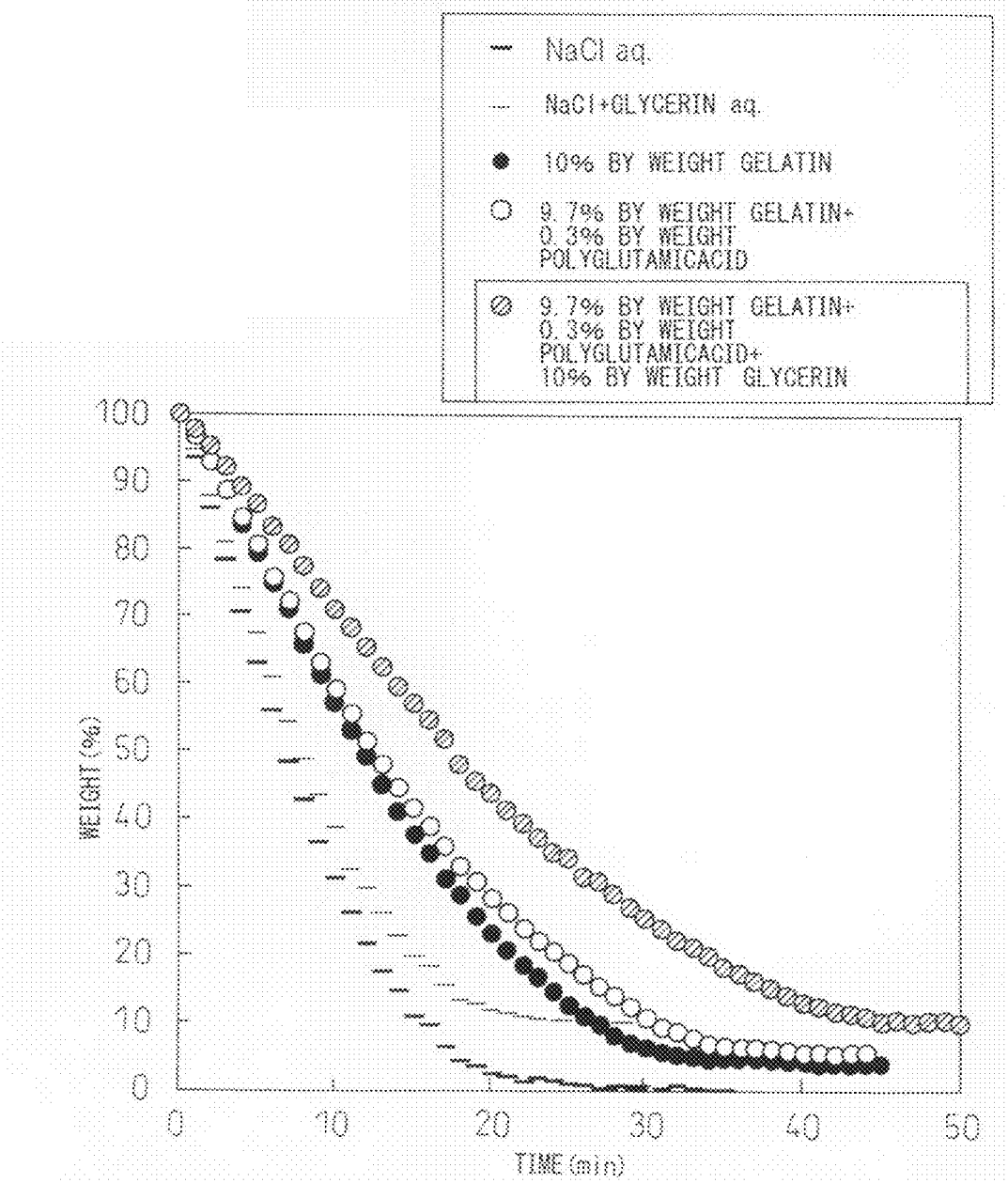

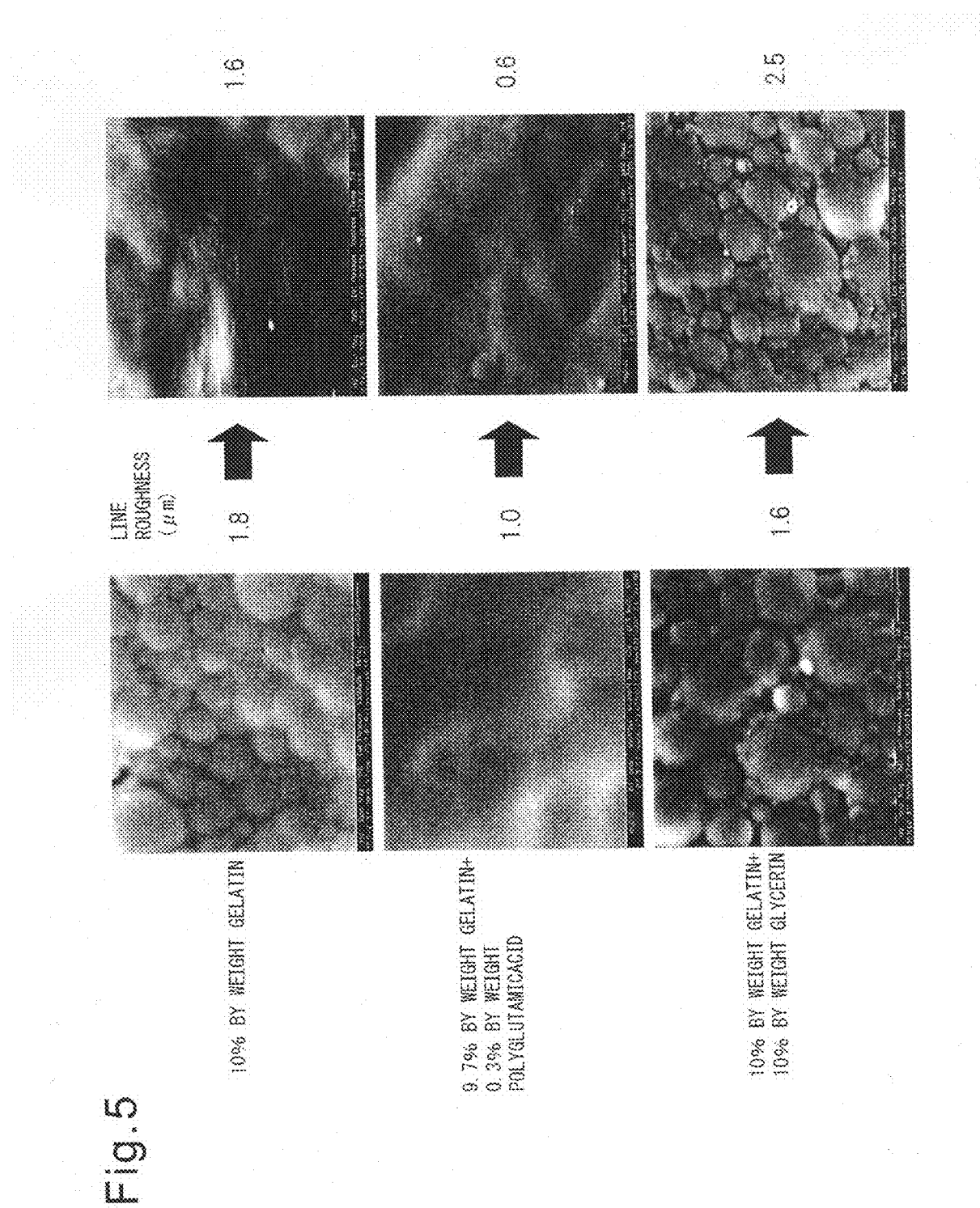

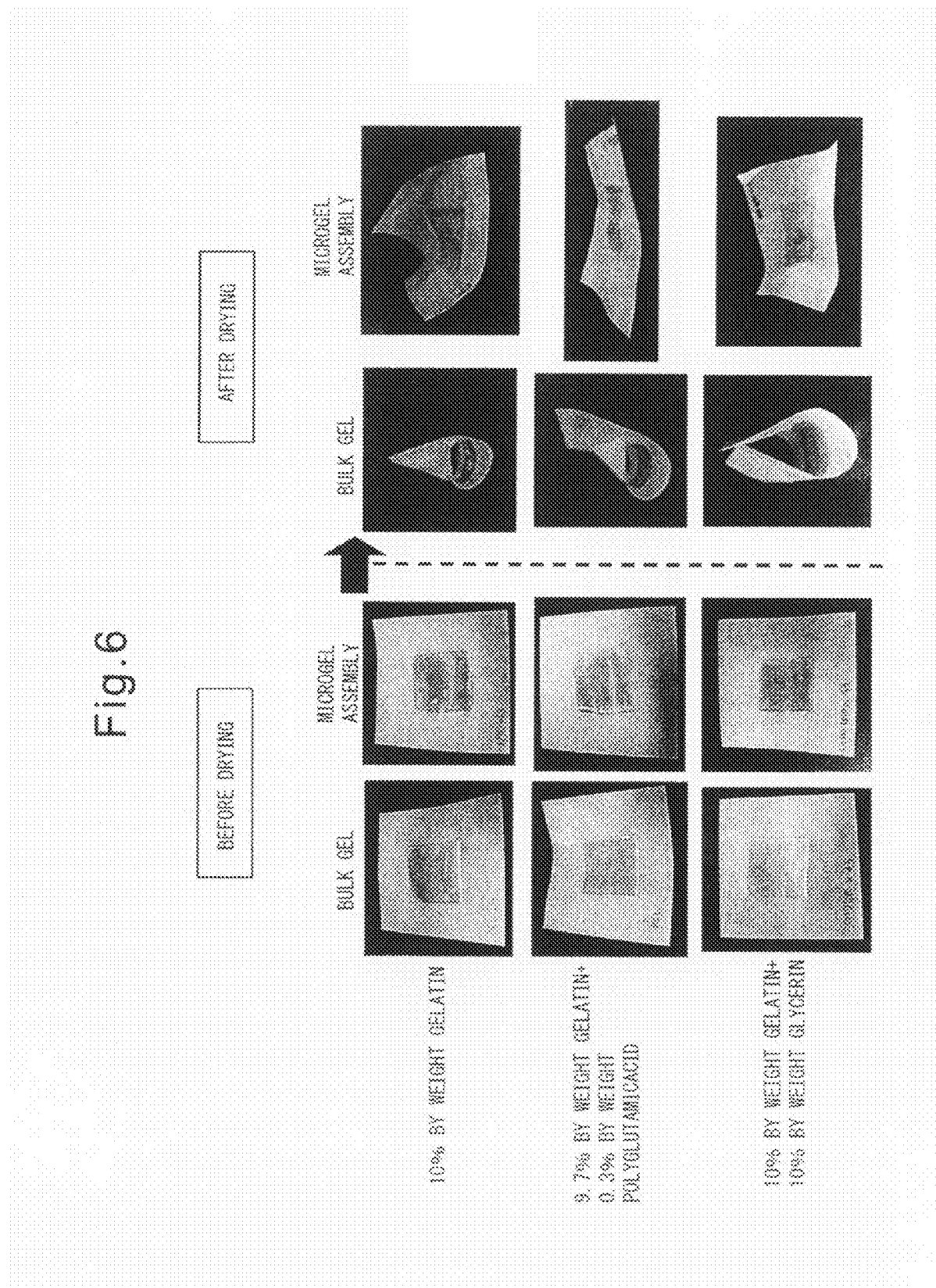

TRANSGLUTAMINASE CROSSLINKED PROTEIN MICROPARTICLE FILM COMPOSITION

CROSS-REFERENCE TO RELATED APPLICATIONS

This application is a National Stage application of PCT/JP2009/050393, filed Jan. 14, 2009, which claims priority from Japanese application JP 2008-006117, filed Jan. 15, 2008.

TECHNICAL FIELD

The present invention relates to a film composition comprising crosslinkable protein microparticles having superior stretchability and flexibility, adequate strength and superior air permeability and moisture evaporation properties, a two-pack-type skin preparation for external use for forming the film composition comprising crosslinkable protein microparticles, and a cosmetic method for correcting irregularities on the skin surface by the use thereof.

BACKGROUND ART

Although numerous cosmetics and cosmetic methods have been developed for improving a person's aesthetic appearance, since it is difficult for existing cosmetics or cosmetic methods to correct prominent irregularities on the skin surface such as deep wrinkles or scars caused by injuries or burns, attempts have been made to correct aesthetic defects by forming a film on the skin.

For example, Japanese Unexamined Patent Publication No. H11-349442 discloses a wrinkle and hair follicle concealing cosmetic comprising a translucent spherical powder and silicone. However, although this cosmetic is considered to be able to correct small surface irregularities such as shallow wrinkles, since this cosmetic composition is not crosslinked and does not have adequate strength with respect to strong force such as when touching with the hands, it is thought to be unable to correct large surface irregularities, such as deep wrinkles and scars.

In addition, Japanese Unexamined Patent Publication No. 2000-16919 discloses a preparation for external use for correcting irregularities on the skin surface, which contains a silicone cosmetic compound, silicone oil and a powder. However, this composition of a preparation for external use is not crosslinked, does not have adequate strength with respect to strong force such as when touching with the hands, and does not have adequate stretchability or flexibility.

Patent Document 1: Japanese. Unexamined Patent Publication No. H11-349442
Patent Document 2: Japanese Unexamined Patent Publication No. 2000-16919

DISCLOSURE OF THE INVENTION

Problems to be Solved by the Invention

At locations such as the face where the skin deforms and moves easily, a coating composition is required to have stretchability and flexibility in order to follow those deformations. However, in the film compositions prepared from polymer aqueous solutions as disclosed in the aforementioned publications, the ability to follow such deformations is inadequate. In addition, in the case of applying to locations frequently touched with hands, such as face, the film is also required to have adequate strength with respect to such physical force. In addition, it is necessary to form a thick film in order to correct large deformations of the skin in the manner of deep wrinkles and scars caused by injuries or burns, while superior air permeability and moisture evaporation properties are required by the film in order to maintain the skin in a healthy state.

Means for Solving the Problems

The present invention provides an effective film composition for correcting surface irregularities, in particular irregularities on skin surface, which has improved stretchability and flexibility as a result of crosslinkable protein microparticles in the film composition being crosslinked by transglutaminase, as well as superior air permeability and moisture evaporation properties, a two-pack-type skin preparation for external use for forming the film composition, and a cosmetic method for correcting irregularities on the skin surface by using the same. Specific aspects of the present invention for solving these problems are as indicated below.

1. A film composition comprising crosslinkable protein microparticles, wherein the crosslinkable protein microparticles are mutually crosslinked by transglutaminase.
2. The aforementioned film composition, wherein the crosslinkable protein microparticles are emulsion particles.
3. The aforementioned film composition, wherein the crosslinkable protein emulsion particles are water-in-oil emulsion particles.
4. The aforementioned film composition, wherein the crosslinkable protein is gelatin, collagen or casein.
5. The aforementioned film composition, wherein the particle diameter of the crosslinkable protein microparticles is 1 to 30 μm.
6. The aforementioned film composition, wherein the ratio of the crosslinkable protein component in the film composition is 1 to 20% by weight.
7. The aforementioned film composition, wherein the ratio of the crosslinkable protein component in the film composition is 5 to 15% by weight.
8. The aforementioned film composition, wherein the ratio of the crosslinkable protein component in the film composition is 8 to 12% by weight.
9. The aforementioned film composition, wherein the amount of transglutaminase for mutually crosslinking the crosslinkable protein microparticles is 1 to 20 U per 1 g of crosslinkable protein component.
10. The aforementioned film composition, wherein the amount of transglutaminase for mutually crosslinking the crosslinkable protein microparticles is 1.5 to 10 U per 1 g of crosslinkable protein component.
11. The aforementioned film composition, wherein the amount of transglutaminase for mutually crosslinking the crosslinkable protein microparticles is 5 to 10 U per 1 g of crosslinkable protein component.
12. The aforementioned film composition, which is used to correct surface irregularities.
13. The aforementioned film composition, wherein the crosslinkable protein microparticles further contain an anionic polymer component.
14. The aforementioned film composition, wherein the anionic polymer component is polyglutamic acid.
15. The aforementioned film composition, wherein the ratio of the anionic polymer component in the film composition is 0.01 to 0.5% by weight.

16. The aforementioned film composition, wherein the crosslinkable protein microparticles further contain a polyvalent alcohol component.

17. The aforementioned film composition, wherein the polyvalent alcohol component is glycerin.

18. The aforementioned film composition, wherein the ratio of the polyvalent alcohol component in the film composition is 1 to 50% by weight.

19. A two-pack-type skin preparation for external use for forming a film on the surface of skin by mutually crosslinking crosslinkable protein microparticles, comprising a first agent containing crosslinkable protein microparticles and a second agent containing transglutaminase.

20. The aforementioned two-pack-type skin preparation for external use, wherein the crosslinkable protein microparticles contained in the first agent are emulsion particles.

21. The aforementioned two-pack-type skin preparation for external use, wherein the crosslinkable protein emulsion particles contained in the first agent are water-in-oil emulsion particles.

22. The aforementioned two-pack-type skin preparation for external use, wherein the microparticles in the first agent further contain an anionic polymer component.

23. The aforementioned two-pack-type skin preparation for external use, wherein the anionic polymer component is polyglutamic acid.

24. The aforementioned two-pack-type skin preparation for external use, wherein the microparticles of the first agent further contain a polyvalent alcohol component.

25. The aforementioned two-pack-type skin preparation for external use, wherein the polyvalent alcohol component is glycerin.

26. A cosmetic method for correcting irregularities on the skin surface, comprising: forming a film on the skin surface in which crosslinkable protein microparticles are mutually crosslinked by applying a mixture of a first agent containing the crosslinkable protein microparticles and a second agent containing transglutaminase to a desired location on the skin surface, or mixing the first agent and the second agent by separately applying to a desired location on the skin surface, and then drying the mixture of the first agent and the second agent at the location.

27. The aforementioned cosmetic method, wherein the crosslinkable protein microparticles contained in the first agent are emulsion particles.

28. The aforementioned cosmetic method, wherein the crosslinkable protein emulsion particles contained in the first agent are water-in-oil emulsion particles.

29. The aforementioned cosmetic method, wherein the microparticles in the first agent further contain an anionic polymer component.

30. The aforementioned cosmetic method, wherein the anionic polymer component is polyglutamic acid.

31. The aforementioned cosmetic method, wherein the microparticles in the first agent further contain a polyvalent alcohol component.

32. The aforementioned cosmetic method, wherein the polyvalent alcohol component is glycerin.

BRIEF DESCRIPTION OF THE DRAWINGS

FIG. 4 is a graph indicating moisture evaporation rates of microparticle dispersions (of microparticles A, B and C) in comparison with controls (aqueous sodium chloride solution and aqueous sodium chloride+glycerin solution).

FIG. 5 shows environmental scanning electron micrographs (ESEM) indicating changes is surface shape of a microparticle assembly accompanying drying.

FIG. 6 shows photographs comparing shrinkage of various bulk gels and microparticle assemblies on drug wrapping paper accompanying drying.

BEST MODE FOR CARRYING OUT THE INVENTION

Figure 1:
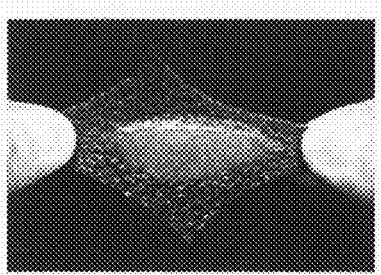
FIG. 1 shows photographs indicating the stretchability and flexibility of a gelatin particulate film prepared according to a water-in-oil emulsion method.
Figure 1:
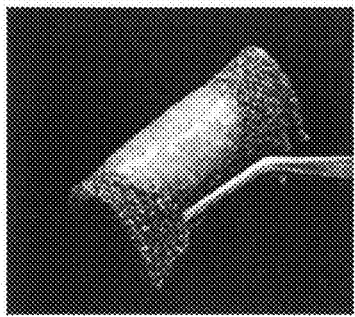

The term "crosslinkable protein" used in the present description refers to a gelable protein having high crosslinking ability, and is preferably a protein capable of being crosslinked by transglutaminase. Examples of such crosslinkable proteins include gelatin, collagen and casein.

The term "microparticle" used in the present description is intended to include both the crosslinked particles and non-crosslinking particles of the crosslinkable protein. The crosslinked particles refer to particles which have been gelled in a solvent by crosslinking, while non-crosslinking particles refer to emulsion particles which are not gelled in a solvent by crosslinking.

In one aspect of the present invention, a film composition comprising crosslinkable protein microparticles is provided. The crosslinkable protein microparticles are preferably emulsion particles. In addition, the crosslinkable protein emulsion particles are preferably water-in-oil emulsion particles. The water-in-oil emulsion particles have a micelle structure in which the oily phase consists of a continuous phase (external phase), while the dispersed phase (internal phase) consists of an aqueous solution of crosslinkable protein.

The water-in-oil emulsion particles of the crosslinkable protein are formed by adding solution of a crosslinkable protein such as gelatin, collagen or casein to a dispersed system (oil), and further adding a surfactant as necessary by mechanical means such as an ultrasonic mixer, propeller stirrer, paddle mixer, homomixer or colloid mill.

According to the present invention, the oil used to form the emulsion may be any oil commonly used to form water-in-oil emulsions in the art, provided that it is not harmful to the human body, examples of which include isododecane, isohexadecane, linear polysiloxanes, cyclic polysiloxanes, modified polysiloxanes, squalane, isopropyl myristate, cetyl octanoate, isopropyl palmitate, glycerol trioctanoate, pentaerythritol tetra-2-ethylhexanoate, diisobutyl adipate, di-2-ethylhexyl sebacate, olive oil, jojoba oil and germ oil. Decamethylcyclopentasiloxane is particularly preferable.

The particle diameter of the crosslinkable protein microparticles, such as emulsion particles, is 0.1 to 100 μm, preferably 0.1 to 80 μm and more preferably 1 to 30 μm. Microparticle diameter can be measured using means commonly used in the art, such as the PAR-IIIs Photon Correlater (Otsuka Electronics), by laser light scattering, the Coulter counter method or the like.

The microparticles can be crosslinked and polymerized to form a coating film comprising crosslinkable protein microparticles by adding transglutaminase to the crosslinkable protein microparticles such as emulsion particles, and allowing to react under optimum conditions, for example at room temperature to 45° C., preferably 30 to 40° C. and most preferably at body temperature, for 5 minutes to 1 hours and preferably for 5 to 30 minutes. Since a gel film containing microparticles obtained in this manner has numerous gaps between the protein microparticles, the gel film can have superior air permeability and moisture evaporation properties as compared with bulk gel. Further, as a result of crosslinking between particles, the gel film having stretchability, flexibility and strength sufficient for applying to skin can be obtained.

Transglutaminases belong to a family of calcium- and thiol-dependent acyl transferases, which are widely present throughout nature. These enzymes catalyze the formation of amide bonds between γ-carboxamide groups of peptide-bound glutamine residues and primary amino groups of various compounds such as ε-amino groups of lysine present in specific proteins, and are widely used for post-translation modification of proteins and for crosslinking and polymerizing proteins by incorporating amines.

There are no particular limitations on the source of the transglutaminase used in the present invention, and may be, for example, microbial transglutaminase, mammalian transglutaminase, fish transglutaminase or derivatives thereof. These transglutaminases are commercially available, or can be purchased from e.g., Ajinomoto Co., Inc. under the product name "Activa".

The ratio of the crosslinkable protein component in the film composition of the present invention has an effect on the hardness of the film composition, namely on such factors as stretchability, flexibility and strength. The ratio of the crosslinkable protein component in the film composition suitable for application to skin is 1 to 20% by weight, preferably 5 to 15% by weight, and more preferably 8 to 12% by weight.

In addition, the amount of transglutaminase added in order to crosslink the crosslinkable protein microparticles has an effect on the degree of crosslinking of the protein component. The amount of transglutaminase for suitably crosslinking the microparticles is 1 to 20 U, preferably 1.5 to 10 U, and more preferably 5 to 10 U per 1 g of crosslinkable protein component.

In the present description, the abbreviation "U" (for unit) used as a unit of enzyme quantity represents an amount of enzyme activity, and 1 U refers to the amount of enzyme capable of changing 1 μmol of substrate (in the present invention, a crosslinkable protein such as gelatin, collagen or casein) per minute under optimum conditions.

Although the microparticles are mainly comprising crosslinkable protein, a portion of a crosslinkable protein polymer composition can be substituted with an anionic polymer by adding the anionic polymer together with the crosslinkable protein component to a water-swelling solvent (e.g., an aqueous sodium chloride solution) at the stage of preparing the crosslinkable protein microparticles. Since anionic polymers have carboxyl groups and the like in a side chain thereof, the properties of the microparticulate film composition of the present invention can be further improved by imparting characteristics of those functional groups. Examples of properties that are improved include increased retention of substances having the opposite potential of the anionic polymer (e.g., cationic dye), inhibition of release of gel-contained substances caused by concentration gradients, enhanced pliability of the film composition, enhanced crack resistance to bending, improved response to pulling, and improved gel swellability due to repulsion of ion groups derived from the anionic polymer.

Although there are no particular limitations on the anionic polymer (the molecular weight of the polymer is 10,000 to 10,000,000, preferably 100,000 to 5,000,000 and more preferably 500,000 to 1,000,000 as measured by static light scattering), provided that it is not harmful to the human body, it is preferably an anionic polyamino acid such as polyglutamic acid or polyaspartic acid, an anionic polysaccharide such as agar, hyaluronic acid, chondroitin sulfate, succinoglucan, gum arabic, xanthan gum or carboxymethyl cellulose, or a polyacrylic acid, and particularly preferably polyglutamic acid.

The ratio of the anionic polymer component in the film composition is 0.01 to 0.5% by weight, preferably 0.01 to 0.5% by weight, and more preferably about 0.2 to 0.4% by weight.

Further, during preparation of the crosslinkable protein microparticles, a polyvalent alcohol component can be contained as a swelling solvent of the crosslinkable protein microparticles by adding a polyvalent alcohol to a water-swelling solvent (e.g., aqueous sodium chloride solution) of the crosslinkable protein microparticles. Since polyvalent alcohols typically have high affinity for water, they are able to remain within the microparticles without evaporating even if evaporation of the microparticle swelling solvent has reached equilibrium. Thus, moisture evaporation of the film composition can be inhibited and moisture retention of the film composition of the present invention can be improved by containing a polyvalent alcohol component in the crosslinkable protein microparticles.

There are no particular limitations on the polyvalent alcohol, and may be any polyvalent alcohol commonly used as a moisture retention agent in the art, examples of which include glycerin, xylitol, diglycerin, dipropylene glycol, sorbitol, sodium DL-pyrrolidone carboxylate, propylene glycol, butylene glycol, polyethylene glycol, polyglycerin, polyoxyethylene methyl glucoside, maltitol, mannitol and polyvinyl alcohol. Glycerin is used preferably.

The ratio of the polyvalent alcohol component in the film composition is 1 to 50% by weight, preferably 3 to 30% by weight, and more preferably about 5 to 15% by weight.

A film composition obtained in this manner can be applied to correct a surface irregularity, e.g., an irregularity on the skin surface, examples of which include keloid scars caused by burns, skin graft scars, surgical scars, deep wrinkles, deep injury scars, acne scars, large hair follicles and small wrinkles. In this manner, the film composition of the present invention is able to improve aesthetic appearance by correcting irregularities on the skin surface by applying to a location of an irregularity on the skin surface. Since the film composition of the present invention is able to follow movement of the skin and ensure air permeability and moisture evaporation properties through gaps formed between particles, it is able to maintain the skin in a healthy state. Therefore, the film composition of the present invention can be used as, in particular, a coating film for correcting irregularities on the skin surface, and can be provided in a disposable form or the like.

In the present description, a "film composition" and an "assembly" are both used with the same meaning, and refer to an assembly in which crosslinkable protein microparticles are mutually crosslinked by transglutaminase regardless of thickness, size and the like.

In another aspect of the present invention, a two-pack-type skin preparation for external use for forming a film on the skin surface by mutually crosslinking crosslinkable protein microparticles, preferably emulsion particles, is provided. The two-pack-type skin preparation for external use comprises a first agent containing crosslinkable protein microparticles, preferably emulsion particles, and a second agent containing transglutaminase. In the first agent, the crosslinkable protein component is contained at a ratio of about 1 to 20% by weight, preferably 3 to 10% by weight, and more preferably 3 to 5% by weight. In addition, the microparticles in the first agent may further contain an anionic polymer component and/or polyvalent alcohol component. Preferable specific examples and concentrations thereof are as previously described. In the second agent, in the case of being applied, the amount of transglutaminase is about 1 to 20 U, preferably 2.5 to 10 U and more preferably 5 to 10 U per 1 g of the crosslinkable protein component.

The first and/or second agents can both be formulated in a dosage form which can be easily applied to skin. For example, they can be formulated as a lotion preparation, emulsion preparation, cream preparation, ointment preparation, plaster preparation or the like.

The crosslinkable protein microparticles, such as emulsion particles, can be dissolved in a solvent in order to formulate the first agent as one of the preparation forms described above. Examples of solvents for the first agent include linear polysiloxanes, cyclic polysiloxanes, modified polysiloxanes, squalane, isopropyl myristate, cetyl octanoate, isopropyl palmitate, glycerol trioctanoate, pentaerythritol tetra-2-ethylhexanoate, diisobutyl adipate, di-2-ethylhexyl sebacate, olive oil, jojoba oil and germ oil. The second agent can also be formulated by dissolving crystals of transglutaminase in a solvent. Examples of solvents for the second agent include sterile water and buffer solutions.

In preparing the first agent and/or second agent, vehicles, fragrances, oils, surfactants, preservatives, metal ion chelating agents, water-soluble polymers, thickeners, powdered components, ultraviolet protectors, moisturizers, pharmaceutically active ingredients, antioxidants, pH adjusters, cleaning agents, drying agents or emulsifiers and the like commonly used in the art can be optionally blended, provided that they do not inhibit the effects of the present invention.

The two-pack-type skin preparation for external use is preferably provided as a kit comprising the first agent and the second agent. The kit preferably contains instructions that clearly explain handling of the first agent and the second agent.

In still another aspect thereof, a cosmetic method for correcting irregularities on skin surface is provided. In this cosmetic method, a first agent containing crosslinkable protein microparticles, preferably emulsion particles, and a second agent containing transglutaminase are mixed, the mixture is applied to a desired location on the skin, such as an irregularity on the surface of the skin, examples of which include surface irregularities on the face, keloid scars caused by burns, skin graft scars, surgical scars, deep wrinkles, deep injury scars, acne scars, large hair follicles and small wrinkles, or the first agent and the second agent are separately applied to the aforementioned desired location and mixed at the applied location followed by drying the mixture of the first agent and the second agent under optimum conditions, such as a temperature of room temperature to 45° C., preferably 30 to 45° C. and most preferably body temperature and a duration of 5 minutes to 1 hour and preferably 5 to 30 minutes, to form a film in which the crosslinkable protein microparticles are mutually crosslinked on the skin surface to enable correction of irregularities on the skin surface. According to such a cosmetic method, a coating film can be provided that not only is able to improve aesthetic appearance by correcting irregularities on the skin surface, but also follow the movement of skin as well as demonstrate superior air permeability and moisture evaporation properties.

Example 1

Preparation Method of Gelatin Particles by W/O Emulsion Method

Preparation of Non-Crosslinking Gelatin Particles 9 ml of an aqueous solution of 5% gelatin (GSB, Nippi, bovine skin/osseous gelatin, jelly strength: 260 to 290 g, viscosity: 3.0 to 4.0 mPa) were added to 21 ml of decamethylcyclopentasiloxane to obtain a W/O emulsion by ultrasonic dispersion. The precipitated particles were recovered with a pipette to obtain non-crosslinking gelatin particles.

Film Formation of Gelatin Particles by W/O Emulsion Method

3 U of transglutaminase (Ajinomoto, molecular weight: 38,000) were added to 1 ml of the aforementioned non-crosslinking gelatin particles and mixed, followed by opening a hole having a diameter of about 2 cm and a thickness of about 3 mm in a skin substitute in the form of a polyurethane sponge, dropping the mixture therein and allowing the mixture to spread within the hole. Subsequently, the mixture was allowed to react for 1 hour at a relative humidity of 65% and temperature of 40° C. to obtain a gel particle film.

Deformability of Gelatin Microparticle Film Composition

As shown in FIG. 1, in the case of stretching and bending polyurethane to which the crosslinkable protein emulsion particle film of the present invention has been applied, the film composition followed these movements in both directions. Thus, the microparticle film of the present invention was confirmed to have high stretchability and flexibility, and able to adequately follow deformation of the skin.

Example 2

Preparation of Microparticle Assembly A and Bulk Gel A

10% by Weight Gelatin

10 U of transglutaminase per 1 g of gelatin were added to non-crosslinking emulsion particles containing 10% by weight gelatin which were prepared by a W/O emulsion method in the same manner as Example 1 to internally crosslink the emulsion particles, followed by dispersing in 10 mM aqueous sodium chloride solution to obtain crosslinked gelatin particles, which had reached swelling equilibrium (Microparticles A). The crosslinked gelatin particles were recovered, transglutaminase was additionally added in order to inter-crosslink the particles, and then a microparticle assembly (Microparticle Assembly A) was obtained. On the other hand, a bulk gel containing 10% by weight gelatin was prepared according to usual methods, followed by immersing in 10 mM aqueous sodium chloride solution and allowing to reach swelling equilibrium (Bulk Gel A).

Preparation of Microparticle Assembly B and Bulk Gel B by Addition of Glycerin to Swelling Solvent (10% by Weight Gelatin+10% by Weight Glycerin)

10 U of transglutaminase per 1 g of gelatin were added to non-crosslinking emulsion particles containing 10% by weight gelatin which were prepared by a W/O emulsion method in the same manner as Example 1 to internally crosslink the emulsion particles, followed by dispersing in 10 mM aqueous sodium chloride solution containing 10% by weight of glycerin (Wako Pure Chemical Industries) to obtain crosslinked gelatin particles which had reached swelling equilibrium (Microparticles B). The crosslinked gelatin particles were recovered, and transglutaminase was additionally added in order to inter-crosslink the particles, and then a microparticle assembly (Microparticle Assembly B) was obtained. On the other hand, a bulk gel containing 10% by weight gelatin was prepared according to usual methods, followed by immersing in 10 mM aqueous sodium chloride solution containing 10% by weight of glycerin and allowing to reach swelling equilibrium (Bulk Gel B).

Preparation of Microparticle Assembly C and Bulk Gel C by Addition of Polyglutamic Acid (PGA) to Swelling Solvent (9.7% by Weight Gelatin+0.3% by Weight Polyglutamic Acid)

Non-crosslinking emulsion particles comprising 9.7% by weight of gelatin and 0.3% by weight of polyglutamic acid were prepared by further adding polyglutamic acid (molecular weight: about 800,000) to a gelatin solution according to a W/O emulsion method in the same manner as Example 1, and 10 U of transglutaminase per 1 g of gelatin were added in order to internally crosslink the emulsion particles. The particles were then dispersed in 10 mM aqueous sodium chloride solution to obtain crosslinked gelatin particles which had reached swelling equilibrium (Microparticles C). The crosslinked gelatin particles were recovered, and transglutaminase was additionally added in order to inter-crosslink the particles, and then a microparticle assembly (Microparticle Assembly C) was obtained. On the other hand, a bulk gel comprising 9.7% by weight of gelatin and 0.3% by weight of PGA was prepared according to usual methods, followed by immersing in 10 mM aqueous sodium chloride solution and allowing to reach swelling equilibrium (Bulk Gel C).

The degree of swelling of the aforementioned microparticle assemblies (A and C) and bulk gels (A and C) relative to pH was measured, and pH curves were prepared and compared by plotting the degree of swelling on the vertical axis and pH on the horizontal axis. For both the microparticle assemblies and bulk gels, the swelling curves shifted towards lower pH in the case of containing polyglutamic acid. Therefore, it was confirmed that the microparticle assemblies and bulk gels demonstrate similar swelling behavior. In addition, when the Z potentials of the microparticles (A and C) relative to pH were measured, since the swelling curves shifted towards lower pH in the case of containing polyglutamic acid, it was confirmed that the properties of the microparticles were maintained even after having been formed into assemblies. In addition, an evaluation of salt concentration responsiveness of swelling and contraction of the gels confirmed that the microparticles and microparticle assemblies demonstrate corresponding responses.

Example 3

Dye Adsorption and Release Behavior

A gel (18×18×2 mm) at swelling equilibrium at pH 6 was immersed at a prescribed concentration in a solution containing cationic methylene blue dihydrate to trihydrate (MB, Junsei Chemical) at 56 µM (ionic strength: 0.01, 15 mL, per measurement), and the time the gel was immersed was defined as time 0. Absorbance was then measured over time while gently stirring with a stirrer (620 nm, MPR A4i Microplate Reader, Tosoh), and the amount of MB incorporated in the gel was calculated by subtracting the concentration of the external liquid from the initial concentration. Next, the gel in which MB had been adsorbed was immersed in a solution not containing MB at pH 2 and absorbance was measured in the same manner to calculate the amount of MB incorporated in the gel.

Figure 2:
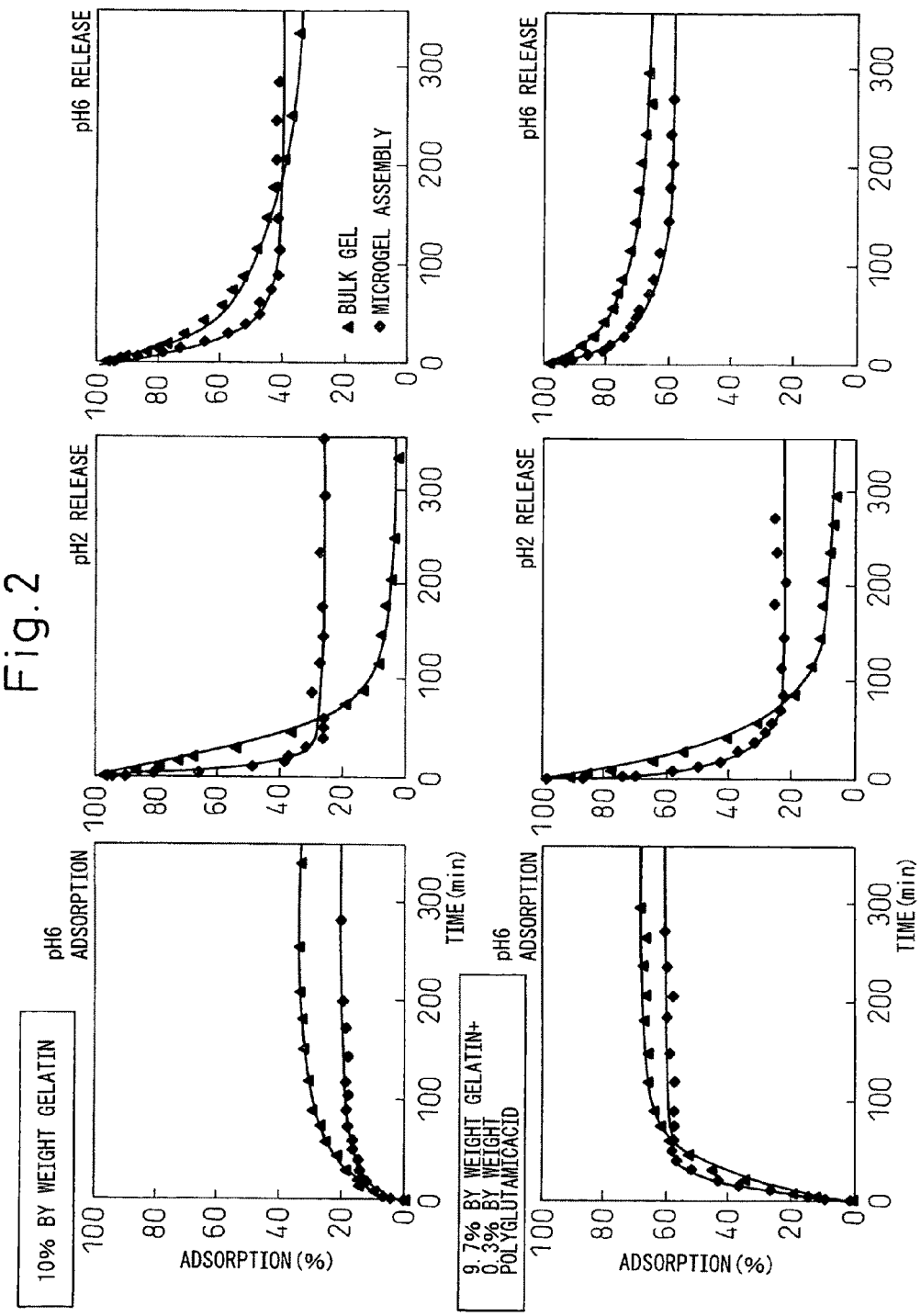
FIG. 2 shows graphs indicating changes in adsorption and release times of methylene blue in a microparticle assembly A, bulk gel A, microparticle assembly C and bulk gel C.

As shown in FIG. 2, Microparticle Assembly A demonstrated faster responsiveness than Bulk Gel A. On the other hand, gels in which PGA had been introduced into the gel (Microparticle Assembly C and Bulk Gel C) demonstrated an increase in the adsorbed amount of MB in comparison with gels only containing gelatin (Microparticle Assembly A and Bulk Gel A). In addition, since there were hardly any differences in the amino group content between the gels in which PGA had been introduced into the gel (Microparticle Assembly C and Bulk Gel C) and the gels only containing gelatin (Microparticle Assembly A and Bulk Gel A), although there are no large differences in release behavior in a system in which pH is changed from 6 to 2, release of MB due to the presence of a concentration gradient was inhibited in a system in which MB is released at pH 6 under the same adsorption conditions. Although a concentration gradient is thought to serve as the main driving force behind the release of gel even under conditions in which strong electrostatic attraction acts between the gel and MB in the case of ordinary gelatin gels, as a result of introducing PGA into the gel, an action that causes MB adsorbed by electrostatic attraction to remain within the gel increases, thereby inhibiting the release of gel driven by the concentration gradient.

Example 4

Gel Dynamic Characteristics

Figure 3:
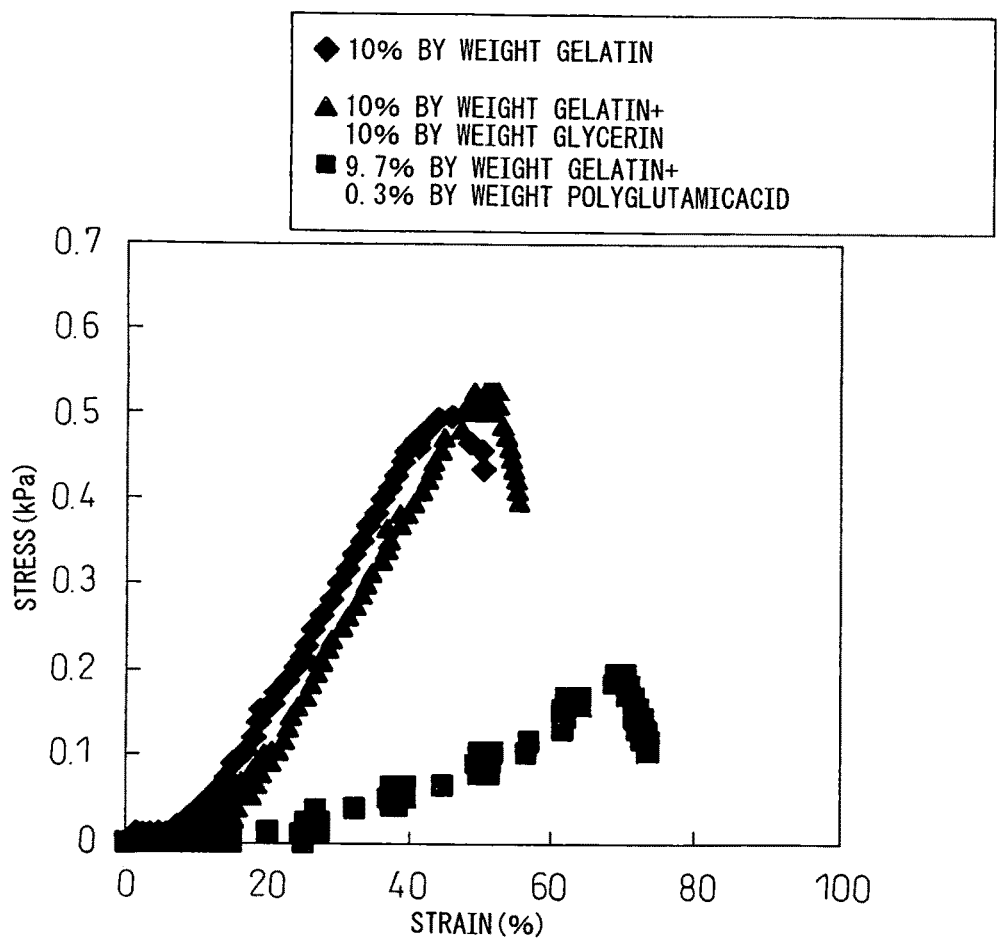
FIG. 3 is a graph indicating stress-strain curves of microparticle assemblies A, B and C.

Stress-strain measurements were carried out on each of the gels prepared in Example 2 using the FUDOH Rheometer NRM-2010J-CW (Rheotech). Measurement conditions consisted of a plunger diameter of 3.015 mm (bulk gel measurement) or 10.05 mm (microgel assembly measurement), a cylindrical sample measuring 18 mm in diameter and 10 mm high, the use of swollen gel, and measuring rupture strength by causing the plunger to penetrate into the sample. Strain was calculated as (plunger penetration depth/sample initial thickness)×100 (%). As a result, gels in which PGA was introduced into the gel (Microparticle Assembly C and Bulk Gel C) demonstrated decreased strength and increased pliancy as compared with other gels (FIG. 3). This is thought to be due to the highly ionic PGA molecular chains intermingling with gelatin chains resulting in a decrease in intermolecular action among the gelatin chains. As a result, the enzyme reaction was inhibited by electrostatic repulsion of the highly ionic PGA molecular chains, thereby causing crosslinking between particles to be weaker than that of the Microparticle Assembly A, while the increase in pliancy was thought to be due to the higher degree of swelling of the microgel.

Example 5

Gel Bending and Pulling Following Ability

Each of the microparticle assemblies prepared in Example 2 were similarly prepared on a polyurethane sponge, and the ability of each microparticle assembly adhered to the urethane sponge to follow bending and pulling of the sponge was examined by deforming the shape of the sponge. As a result, the microparticle assembly in which PGA was introduced into the gelatin (Microparticle Assembly C) demonstrated superior ability to follow bending and pulling of the sponge in comparison with the microparticle assembly only containing gelatin (Microparticle Assembly A).

Example 6

Gel Moisture Evaporation Properties

The weights of 10 µl of controls (aqueous sodium chloride solution and aqueous sodium chloride solution+glycerin) and 1.2% by weight dispersions of each of the microparticles prepared in Example 2 were measured (in a constant temperature, constant humidity chamber at a temperature of 22° C. and relative humidity of 45%) to evaluate moisture evaporation properties of each solution. As a result, microparticles that had reached swelling equilibrium after being dispersed in a 10 mM aqueous sodium chloride solution containing 10% by weight of glycerin (Microparticles B) prominently inhibited moisture evaporation as compared with the other microparticles (FIG. 4).

Example 7

Changes in Shape of Gel Surface Accompanying Drying

The form of the surface of each gel prepared in Example 2 before and after drying was evaluated with an environmental scanning electron microscope (FEI Quanta 200, Nikon Instech, image capturing magnification: ×1,000). Although the microparticle assemblies containing gelatin only and PGA completely collapsed into a spherical shape following drying and gaps between particles were no longer present, in the microparticle assembly containing glycerin, the shape of the particles was determined to be sharply maintained after drying (FIG. 5). In addition, swelling rates of the gel particles can be evaluated numerically by measuring line roughness using a super depth profile measurement microscope (Super Depth Profile Measurement Microscope VK-8500, Keyence). Line roughness refers to a value representing in micrometer units the width by which surface irregularities in the direction of height of a sample surface deviate from a central base line on average. The measurement method consisted of placing the prepared assemblies between slide glasses and measuring swelling either directly or after allowing to dry overnight indoors. Line roughness refers to calculated average roughness (Ra), and was calculated in accordance with the definition of JIS B 0601-1994. Measured values are shown as the average values of 10 measurements. When comparing the line roughness of each microparticle assembly after drying, since the value of the glycerin-containing microparticle assembly was high, gel moisture retention was determined to be improved by addition of glycerin to the swelling solvent, and changes in surface shape of the microparticle assemblies attributable to drying were inhibited.

Example 8

Evaluation of Shrinkage Accompanying Drying

Each of the gels measuring 18×18×1 mm prepared in Example 2 were placed on drug wrapping paper and dried overnight at a relative humidity of 43%. Gel shrinkage accompanying drying was evaluated based on deformation of the drug wrapping paper caused by gel drying. As a result, the microparticle assemblies demonstrated considerably less shrinkage accompanying drying than the bulk gels (FIG. 6). This is thought to be due to the fact that, in contrast to the composite polymers of the bulk gels integrating into a single unit and becoming intermingled, since the microparticle assemblies consist of assemblies of particles on the micrometer order, drying contraction of a single microparticle had little effect on surrounding microparticles, thereby resulting in less deformation overall.

The invention claimed is:

1. A film comprising crosslinkable protein microparticles, wherein the crosslinkable protein microparticles have been mutually crosslinked by transglutaminase.

2. The film according to claim 1, wherein the crosslinkable protein microparticles are emulsion particles.

3. The film according to claim 2, wherein the crosslinkable protein emulsion particles are water-in-oil emulsion particles.

4. The film according to claim 1, wherein the crosslinkable protein is gelatin, collagen or casein.

5. The film according to claim 1, wherein the particle diameter of the crosslinkable protein microparticles is 1 to 30 µm.

6. The film according to claim 1, wherein the ratio of the crosslinkable protein microparticle in the film is 1 to 20% by weight.

7. The film according to claim 6, wherein the ratio of the crosslinkable protein microparticle in the film is 5 to 15% by weight.

8. The film according to claim 7, wherein the ratio of the crosslinkable protein microparticle in the film is 8 to 12% by weight.

9. The film according to claim 1, wherein the amount of transglutaminase for mutually crosslinking the crosslinkable protein microparticles is 1 to 20 U per 1 g of crosslinkable protein component.

10. The film according to claim 9, wherein the amount of transglutaminase for mutually crosslinking the crosslinkable protein microparticles is 1.5 to 10 U per 1 g of crosslinkable protein component.

11. The film according to claim 10, wherein the amount of transglutaminase for mutually crosslinking the crosslinkable protein microparticles is 5 to 10 U per 1 g of crosslinkable protein component.

12. The film according to claim 1, which is used to correct surface irregularities.

13. The film according to claim 1, wherein the crosslinkable protein microparticles further contain an anionic polymer component.

14. The film according to claim 13, wherein the anionic polymer component is polyglutamic acid.

15. The film according to claim 13, wherein the ratio of the anionic polymer component in the film is 0.01 to 0.5% by weight.

16. The film according to claim 1, wherein the crosslinkable protein microparticles further contain a polyvalent alcohol component.

17. The film according to claim 16, wherein the polyvalent alcohol component is glycerin.

18. The film according to claim 16, wherein the ratio of the polyvalent alcohol component in the film is 1 to 50% by weight.

19. A two-pack-type skin preparation for external use for forming a film on the surface of skin by mutually crosslinking crosslinkable protein microparticles, comprising a first agent containing crosslinkable protein microparticles and a second agent containing transglutaminase.

20. The two-pack-type skin preparation for external use according to claim 19, wherein the crosslinkable protein microparticles contained in the first agent are emulsion particles.

21. The two-pack-type skin preparation for external use according to claim 20, wherein the crosslinkable protein emulsion particles contained in the first agent are water-in-oil emulsion particles.

22. The two-pack-type skin preparation for external use according to claim 19, wherein the microparticles in the first agent further contain an anionic polymer component.

23. The two-pack-type skin preparation for external use according to claim 22, wherein the anionic polymer component is polyglutamic acid.

24. The two-pack-type skin preparation for external use according to claim 19, wherein the microparticles of the first agent further contain a polyvalent alcohol component.

25. The two-pack-type skin preparation for external use according to claim 24, wherein the polyvalent alcohol component is glycerin.

* * * * *